(12) United States Patent
Cornils et al.

(10) Patent No.: US 12,127,591 B2
(45) Date of Patent: Oct. 29, 2024

(54) EVAPORATOR DEVICE FOR AN INHALER, CONSUMPTION UNIT, INHALER, AND PRODUCTION METHOD

(71) Applicant: KÖRBER TECHNOLOGIES GMBH, Hamburg (DE)

(72) Inventors: Lasse Cornils, Hamburg (DE); Niklas Romming, Hamburg (DE); Jan Jaklin, Fellbach (DE); Gunnar Niebuhr, Hamburg (DE); Tim Ullner, Hamburg (DE); Thomas Mueller, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 518 days.

(21) Appl. No.: 17/431,956

(22) PCT Filed: Feb. 14, 2020

(86) PCT No.: PCT/EP2020/053879
§ 371 (c)(1),
(2) Date: Aug. 18, 2021

(87) PCT Pub. No.: WO2020/169467
PCT Pub. Date: Aug. 27, 2020

(65) Prior Publication Data
US 2022/0151295 A1    May 19, 2022

(30) Foreign Application Priority Data
Feb. 18, 2019   (DE) ......................... 10 2019 103 987

(51) Int. Cl.
*A24F 40/46*   (2020.01)
*A24F 40/10*   (2020.01)
(Continued)

(52) U.S. Cl.
CPC .............. *A24F 40/46* (2020.01); *A24F 40/10* (2020.01); *A24F 40/42* (2020.01); *A24F 40/44* (2020.01);
(Continued)

(58) Field of Classification Search
CPC ........ A24F 40/10; A24F 40/46; A24F 40/485; A24F 40/44; A24F 40/42; A24F 40/00; A24F 40/40; A24F 40/70
See application file for complete search history.

(56) References Cited

U.S. PATENT DOCUMENTS

| | | |
|---|---|---|
| 8,833,364 B2 | 9/2014 | Buchberger |
| 10,543,323 B2 | 1/2020 | Buchberger |

(Continued)

FOREIGN PATENT DOCUMENTS

| | | |
|---|---|---|
| CN | 102264420 A | 11/2011 |
| CN | 108158040 A | 6/2018 |

(Continued)

OTHER PUBLICATIONS

European Examination report issued by the European Patent Office on Feb. 5, 2024 in parallel European patent application No. 20 705 931.2.

(Continued)

*Primary Examiner* — Truc T Nguyen
(74) *Attorney, Agent, or Firm* — SALIWANCHIK, LLOYD & EISENSCHENK

(57) ABSTRACT

A vaporizer device for an inhaler comprises at least one electric vaporizer for vaporizing liquid fed to the vaporizer, wherein the liquid is transported by capillary forces from an inlet side through at least one liquid channel to an outlet side, where vaporized liquid can be added to an air stream, a carrier retaining the vaporizer, and at least one electrical line electrically contacting the vaporizer. The electrical line (Continued)

comprises a planar contact area, and the vaporizer and the planar contact area of the electrical line are materially and electrically conductively bonded to each other.

24 Claims, 3 Drawing Sheets

(51) Int. Cl.
    *A24F 40/42*     (2020.01)
    *A24F 40/44*     (2020.01)
    *A24F 40/70*     (2020.01)
    *B22F 7/06*     (2006.01)
    *B23K 20/02*     (2006.01)
    *B23K 20/10*     (2006.01)
    *H05B 3/12*     (2006.01)
    *H05B 3/18*     (2006.01)
    *B23K 101/36*     (2006.01)

(52) U.S. Cl.
    CPC .............. *A24F 40/70* (2020.01); *B22F 7/062* (2013.01); *B23K 20/023* (2013.01); *B23K 20/10* (2013.01); *H05B 3/12* (2013.01); *H05B 3/18* (2013.01); *B23K 2101/36* (2018.08); *H05B 2203/016* (2013.01); *H05B 2203/017* (2013.01); *H05B 2203/021* (2013.01)

(56) References Cited

U.S. PATENT DOCUMENTS

| | | |
|---|---|---|
| 2016/0345629 A1 | 12/2016 | Mironov |
| 2018/0064170 A1 | 3/2018 | Peuchert et al. |
| 2018/0242643 A1* | 8/2018 | Silvesstrini .............. H05B 3/34 |
| 2018/0289066 A1* | 10/2018 | Mo ........................ A24F 40/485 |
| 2018/0295888 A1* | 10/2018 | Newcomb ............... A24F 40/40 |
| 2019/0082739 A1* | 3/2019 | Slivestrini ............. A24F 40/485 |
| 2019/0216132 A1* | 7/2019 | Phan ....................... C03C 11/00 |
| 2020/0029619 A1* | 1/2020 | Sundberg .................. A24F 7/02 |
| 2022/0151295 A1* | 5/2022 | Cornils ................... A24F 40/44 |

FOREIGN PATENT DOCUMENTS

| | | |
|---|---|---|
| CN | 108 308 716 A | 7/2018 |
| CN | 207926944 U | 9/2018 |
| DE | 10 2017 111 119 A1 | 11/2018 |
| EP | 2 316 286 A1 | 5/2011 |
| EP | 3 216 359 A1 | 9/2017 |
| JP | 2017-506890 A | 3/2017 |
| WO | WO 2015/117701 A1 | 8/2015 |

OTHER PUBLICATIONS

Japanese Examination report issued by the Japanese Patent Office on Feb. 13, 2024 in parallel Japanese patent application No. 2021-547852.

Examination Report issued by the Chinese Patent Office dated Jun. 5, 2024 in parallel Chinese patent application No. 202080014958.X with an English translation.

* cited by examiner

EVAPORATOR DEVICE FOR AN INHALER, CONSUMPTION UNIT, INHALER, AND PRODUCTION METHOD

CROSS REFERENCE TO RELATED APPLICATIONS

This application is a National Stage Application of International Application Number PCT/EP2020/053879, filed Feb. 14, 2020; which claims priority to German Patent Application No. 10 2019 103 987.8, filed Feb. 18, 2019.

FIELD OF INVENTION

The present invention relates to a vaporizer device for an inhaler, comprising at least one electric vaporizer for vaporizing liquid fed to the vaporizer, wherein the liquid is transported by capillary forces from an inlet side through at least one liquid channel to an outlet side where vaporized liquid can be added to an air stream, a carrier holding the vaporizer, and at least one electric line electrically contacting the vaporizer. The invention also relates to a consumption unit, an inhaler and a method for manufacturing.

BACKGROUND OF THE INVENTION

Conventional inhalers or electronic cigarette products are based on wick-coil technology. Capillary forces transport liquid from a liquid reservoir along a wick until the liquid is heated by an electrically heatable coil and thus vaporized. The wick serves as a liquid-conducting connection between the liquid reservoir and the heating coil, which serves as a vaporizer.

In conventional inhalers, the electrical contacting of the vaporizer is simple due to the wick-coil technology. All that is required is to apply an electric current to the coil. This heats the coil and liquid can vaporize.

A disadvantage of the wick-coil technology is that a lack of liquid supply leads to local overheating, which can produce pollutants. This so-called "dry puff" must be avoided. In addition, such vaporizer units are often leaky due to the manufacturing process, so that liquid can escape in an undesired manner, for example via the air supply and/or vapor exhaust.

To avoid the problems of the wick-coil technology, generic vaporizers are used that utilize the technology disclosed in DE 10 2017 111 119 A1. Thereby, the liquid is transported by capillary forces from an inlet side through a liquid channel to an outlet side, where vaporized liquid can be added to an air stream as vapor and/or aerosol. The vaporizer is electrically connectable to an energy source via an electrical line. However, the connection of the vaporizer to the electrical line is not described in the cited prior art.

It is the task of the invention to provide a vaporizer device with a reliable and effective electrical connection to the vaporizer.

The task is solved by the features of the independent claims.

BRIEF SUMMARY OF THE INVENTION

According to the invention, it is proposed that the electrical line comprises a planar contact area. The contact areas are areas of the electrical line provided for electrically conductive and materially bonding. The planar contact area of the electrical line improves the geometry of the bond provided between the electrical line and the vaporizer. In particular, the contact area is therefore not point-shaped or curved, as it is the case with an electrical line with a curved and, in particular, round cross-section. Therefore, a reliable electrical connection between the electrical line and the vaporizer can be established in the contact area. Furthermore, due to the planar design of the contact area, an enlarged contact surface for realizing a bond and for current transmission can be achieved. Thus, for example, high transition resistances and associated localized temperature peaks can be avoided.

According to the invention, the vaporizer and the planar contact area of the electrical line are bonded materially and electrically conductive to each other to provide a reliable bond between the electrical line and the vaporizer. In addition, the materially bonded compound can retain the vaporizer on the carrier and/or support the retainer of the vaporizer on the carrier. The materially bonded compound comprising the electrical line and the vaporizer allows for precise electrical contacting, placement, and retaining of the vaporizer device components during production and/or assembly of the vaporizer device.

Preferably, the outer shape of the vaporizer is block-shaped, and one side of the vaporizer is bonded to the electrical line in a planar manner to allow the electrical bond between the electrical line and the vaporizer to be effectively designed and the contact area to be effectively utilized. Advantageously, the vaporizer is bonded to the electrical line on exactly one of its sides, for example the inlet side or the outlet side, in order to realize the simplest possible geometry of the vaporizing device. However, it is also possible that, for example, two sides of the vaporizer, in particular opposite each other, are each bonded to at least one electrical line, for example perpendicular to the outlet side or the inlet side.

Preferably, the carrier retains the electrical line and/or is materially bonded to the electrical line in order to promote an effective and compact design and manufacture of the vaporizer device. A material bond of the electrical line with the carrier leads to a material bonded compound comprising the carrier, the electrical line and the vaporizer.

Advantageously, the vaporizer comprises a base surface, in particular a rectangular base surface, with two opposing edge sections, and each of the opposing edge sections is bonded to an electrical line in order to be able to effectively use the base surface of the vaporizer and to be able to cause electrical resistance between the edge sections and thus heating and vaporization of the liquid.

In a preferred embodiment, at least two electrical lines are provided and the carrier comprises a passage opening between the electrical lines. For example, the vaporizer may be arranged such that the passage opening is arranged on the inlet side of the vaporizer on the carrier. The passage opening allows a wick structure to contact the inlet side of the vaporizer for liquid supply over a surface area. However, the passage opening can also be arranged on the carrier on the outlet side of the vaporizer so that the liquid vaporized by the vaporizer can be added to the air stream flowing over the outlet side.

Preferably, the carrier for retaining the vaporizer comprises a ceramic substrate in order to make the carrier for retaining the vaporizer thermally stable and/or, if appropriate, to thermally decouple the vaporizer from the carrier. The ceramic substrate is chemically and mechanically stable against the temperatures occurring during operation of the vaporizer, for example up to 300° C., and thermal load changes that occur, for example, about 200-2000 times in the life cycle of the vaporizer. The carrier is in contact with the liquid and/or the aerosol respectively the vapor and must therefore be food grade or biocompatible, especially at the temperatures occurring during vaporization, which is favored by the ceramic substrate.

Advantageously, the contact area is made of gold in order to provide a contact area with good electrical conductivity, which is suitable for a material and electrically conductive bond to the vaporizer. The contact area made of gold is chemically stable with respect to the liquid to be vaporized or aerosol or vapor and can be reliably manufactured and processed by methods known in the art.

Preferably, the vaporizer comprises a metallization layer in order to allow preparation with electrical contact surfaces that can be bonded to the electrical line in the contact area. For example, the vaporizer can essentially comprise a silicon block, in particular a doped silicon block, which comprises the metallization layer on the surface. The metallization layer simplifies the electrical and material contacting of the electrical line to the vaporizer.

In an advantageous embodiment, the metallization layer comprises nickel, gold and/or palladium in order to be able to prepare the surface of the vaporizer for the material bond, which surface is electrically conductive and can be processed effectively by known methods.

Preferably, a primer is arranged between the vaporizer and the metallization layer, for example a seed layer of aluminum, on which the metallization layer is deposited advantageously without current.

Advantageously, the electrical bond between the vaporizer and the electrical line comprises an electrical resistance of 5 mΩ to 20 mΩ in order to keep the undesired conversion of electrical energy into heat low compared to the heat generated for vaporization and to be able to supply the vaporizer with sufficient electrical energy at the same time.

Preferably, the material bond is formed at least in part by a first sintered material to allow the bond to be made precisely and effectively. Sintering the material bond saves a considerable amount of time in placing the vaporizers on the carrier. In this embodiment, it is not necessary to electrically bond each contact of the vaporizer individually. A mechanically stable and electrically conductive bond can be made by sintering in a furnace in parallel for a plurality of vaporizers simultaneously.

Preferably, the electrical line is at least partially formed by a second sintered material in order to be able to precisely arrange and effectively manufacture the electrical line.

In an advantageous embodiment, the material bond between the vaporizer and the electrical line comprises an adhesive, in particular an electrically non-conductive adhesive, in order to be able to produce a material bond between the vaporizer and the electrical line. The electrical bond between the electrical line and the vaporizer can be formed and/or arranged independently of the material bond. In particular, the electrical bond can be arranged in a smaller area than the material bond in order to be able to selectively heat and/or electrically contact the vaporizer. At the same time, the vaporizer can be bonded to the carrier in a face-to-face manner.

Preferably, the vaporizer and/or the contact area comprises solder bumps in order to be able to establish a precisely localized and effectively executable electrical bond between the vaporizer and electrical line. In particular, the solder bumps can be gold bumps for advantageous electrical contacting and processing.

Advantageously, the electrical line comprises a coefficient of thermal expansion that differs by less than 10% from the coefficient of thermal expansion of the vaporizer to improve the lifetime of the vaporizer device, since the vaporizer becomes hot up to 300° C. during operation and experiences a thermal load change between ambient temperature and the operating temperature of the vaporizer approximately 200-2000—times in its life cycle. The low difference of less than 10% in the coefficients of thermal expansion results in only a low mechanical stress in the region of the material bond between the electrical line and the vaporizer and thus does not stress the latter mechanically to a critical extent.

According to the invention, a consumption unit for an inhaler comprises the vaporizer device described above and a liquid reservoir, wherein the vaporizer device is connected to the liquid reservoir in a liquid-conducting manner. The inlet side of the vaporizer is connected to the liquid reservoir in a liquid-conducting manner, for example via a wick structure. An inhaler according to the invention comprises the consumption unit and a base unit. The material and electrically conductive bond between the electrical line and the vaporizer means that the consumption unit or the inhaler can be assembled effectively.

A method for manufacturing the vaporizer device described above, includes the following steps: Providing the vaporizer, the carrier and the at least one electrical line, and materially and electrically bonding the vaporizer and the electrical line in a planar contact area of the vaporizer. As preparation for the electrically conductive and material bonding, a corresponding metal coating can optionally be applied to the vaporizer, in particular already on a wafer basis. The contact area of the electrical line is provided as a counterpart for the vaporizer.

Preferably, the bonding comprises a thermocompression process. Advantageously, prior to bonding, the contact area, the carrier and/or the vaporizer are coated in designated bonding areas provided with a sintering paste suitable for thermocompression. The coating of the contact areas with a sintering paste can be carried out, for example, by stenciling, screen printing and/or pad printing.

Advantageously, the bonding comprises an application of ultrasound to promote a friction welding heat for thermomechanical bonding by thermocompression between the electric line and the vaporizer.

Preferably, the bonding includes sintering to provide a simple preparation for the material bond. As preparation for the bonding by sintering, a suitable metallization can already be applied to the contact surfaces of the vaporizers on a wafer basis. The electrical lines themselves can also be produced by sintering. The substance-to-substance compound can be made of a first sintered material and/or the electrical line can be made of a second sintered material. It is also possible to produce the compound and the electrical line in one work step and/or from the same sintered material. Advantageously, the contact area, the carrier and/or the vaporizer are coated with a sintering paste suitable for sintering in provided sintering areas before bonding. For a stable bond between the electrical contact area and the vaporizer, the compound is sintered in a furnace according to the requirements of the sinter paste. Advantageously, sintering is performed without pressure, in particular to avoid mechanical stress on the vaporizer.

Preferably, a plurality of simultaneously processed vaporizers is separated before bonding in order to be able to produce a plurality of vaporizer devices as effectively as possible. The plurality of vaporizers may be in a wafer compound, wherein the wafer compound may form several thousand vaporizers. The wafer compound can be separated by means of a wafer saw, for example, and provide the plurality of separate vaporizers. For this purpose, one vaporizer each can be removed, for example by means of a picking process, from a wafer compound forming a plurality of the vaporizers, and can be electrically conductively and materially bonded to the electrical lines of the carrier, for example by means of flip-chip assembly.

Preferably, a plurality of solder bumps can be applied prior to bonding in order to effectively establish the electrical bond.

Advantageously, the bonding comprises an adhesive bonding, in particular with an electrically non-conductive adhesive, in order to be able to effectively establish the material bond. The adhesive bond can be realized on selected local surfaces, while other surfaces are deliberately not wetted with the electrically non-conductive adhesive, i.e. are not bonded and serve for the electrical connection.

BRIEF DESCRIPTION OF THE FIGURES

The invention is explained in the following by means of preferred embodiments with reference to the accompanying figures. Thereby shows FIG. 1 an exploded view of a vaporizer device and a carrier device.

DETAILED DESCRIPTION

Figure 1:
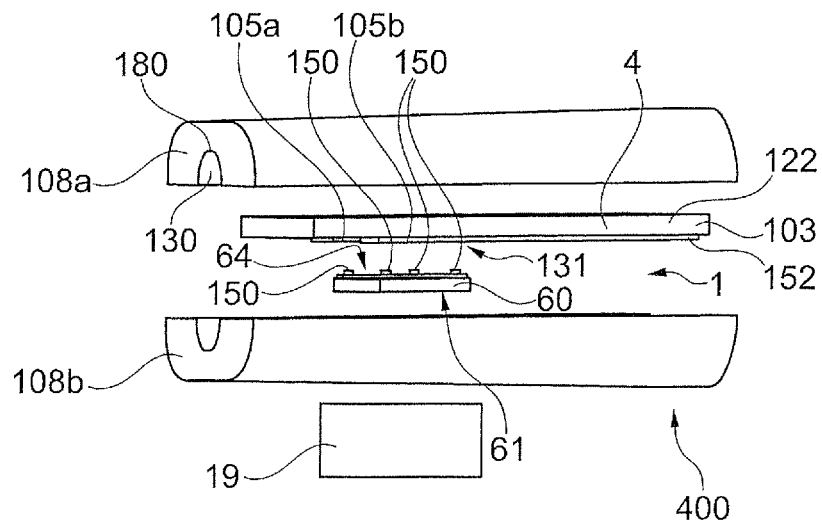

FIG. 1 shows an exploded view of a vaporizer device 1 and a carrier device 400 for an inhaler 10. The vaporizer device 1 comprises an electric vaporizer 60 for vaporizing liquid 50 fed to the vaporizer 60 (see FIGS. 5 and 6). In the assembled state (see FIG. 2), the vaporizer 60 is held by a carrier 4. The vaporizer 60 comprises an outlet side 64 and an inlet side 61 as well as liquid channels 62 located therebetween and is explained in more detail with reference to FIG. 6.

The carrier 4 comprises a ceramic substrate 103, see FIG. 1. In this embodiment, the ceramic substrate 103 is substantially plate-shaped. For example, the ceramic substrate 103 may comprise a zirconium oxide plate or a plate of ceramic, in particular a low temperature co-fired ceramic. The carrier 4 comprises at least one planar portion in which a planar contact area 131 is formed. In this embodiment, the carrier 4 is ceramic. Alternatively, the carrier 4 may comprise a heat resistant plastic and comprise a ceramic vaporizer receptacle.

Advantageously, the substrate 103 has a coefficient of thermal expansion similar to the material of which the vaporizer 60 is primarily made, for example silicon, in particular differing by a maximum of 10%. Thus, mechanical stresses between the substrate 4 and the vaporizer 60 remain low during operation of the vaporizer 60.

Advantageously, the substrate 103 comprises a low thermal conductivity and/or a low heat capacity in order not to transfer the heat intended for vaporization away from the vaporizer 60 and/or to store it in the carrier 4. Thus, the vaporizer 60 is thermally decoupled from the carrier 4 and/or from external components. Due to a low thermal conductivity and/or heat capacity of the carrier 4, the advantageously low thermal inertia of the vaporizer 60 is not impaired. This allows the vaporizer 60 to heat up and/or cool down precisely in time, and in particular quickly, to promote high aerosol quality and precise adjustment of the aerosol quantity.

The vaporizer 60 and the carrier 4 are arranged in such a way that the carrier 4 is electrically and materially bonded to the vaporizer 60 at the outlet side 64 in the assembled state. In order for the vaporizer 60 to add the vaporized liquid to the air stream 34, the carrier 4 comprises a passage opening 104 which is not shown. The passage opening 104 is arranged at the outlet side 64 of the vaporizer 60. Advantageously, the passage opening 104 is at least as large as the area of the vaporizer 60 which is provided with liquid channels 62 (see FIG. 6).

Two electrical lines 105a, 105b are provided on the carrier 4, which are connected to the vaporizer 60 in a materially bonded and electrically conductive manner, see FIG. 1. The electrical lines 105a, 105b are materially bonded to the carrier 4 or are applied on the carrier 4. The electrical lines 105a, 105b may comprise copper, for example.

The electrical lines 105a, 105b comprise a contact area 131 suitable for an electrically conductive and materially bonded connection. The contact area 131 may consist, for example, of gold, advantageously of a layer of gold of preferably 5-50 µm, further preferably 8-20 µm, for example 10 µm.

The compound of carrier 4 and vaporizer 60 is placed, for example, between the two half-shells 108a, 108b, which as a carrier device 400 fulfill, for example, the task of holding the vaporizer device 1 and a wick structure 19 relative to the vaporizer device 1 so that there is a good liquid connection of the vaporizer 60 to an external part, for example a liquid reservoir 18.

The half-shells 108a, 108b are advantageously made of a high-temperature plastic, for example PEEK, which remains mechanically and chemically stable at the temperatures encountered during vaporization.

A recess 180 is provided in the upper shell 108a so that an air channel 130 is formed between the carrier 4 and the upper shell 108a. An air flow 34 flows through the air channel 130 during operation of the inhaler 10. The air flow 34 flows over the outlet side 64 of the vaporizer 60, which adds vaporized liquid 50 as a vapor and/or aerosol to the air flow 34.

An opening, not shown, is provided in the lower shell 108b through which the wick structure 19 extends. The wick structure 19 is connected, on the one hand, to the inlet side 61 of the vaporizer 60 and, on the other hand, to a liquid reservoir 18 in a liquid-conducting manner. The wick structure 19 is explained in more detail with reference to FIGS. 5 and 6.

It is also possible to provide only one electrical line 105a and to conduct the electrical current, for example, via the half-shells 108a, 108b or a housing part (not shown). It is also possible that further electrical contacting of the lines 105a, 105b and/or a secondary air channel 101 is provided in one of the shells 108a, 108b. The carrier device 400 may also comprise a one-piece shell or more than two shell parts.

As it can be seen in FIG. 1, the vaporizer 60 is advantageously a flat heater, in particular a chip-type flat heater. The vaporizer 60 is block-shaped and the outlet side 64 is connected in a planar manner to the electrical lines 105a, 105b in the planar contact area 131 in the assembled state.

Figure 2:
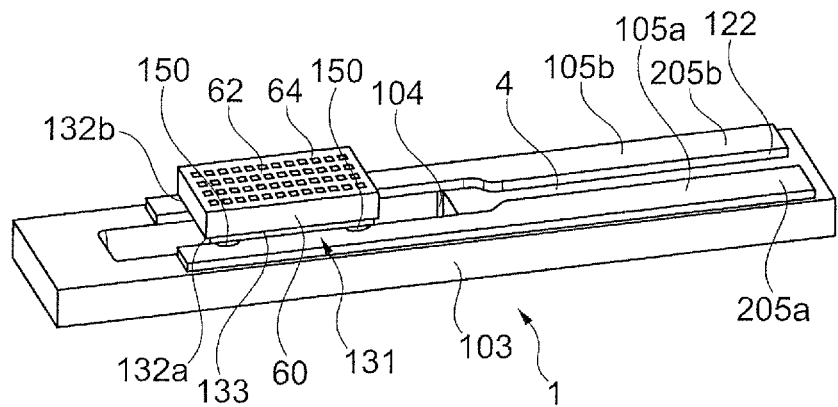
FIG. 2 a perspective view of a vaporizer device in the assembled state.

FIG. 2 shows a perspective view of a vaporizer device 1 in the assembled state. In this embodiment, the inlet side 61 of the vaporizer 60 is connected to the electrical lines 105a, 105b in a planar, electrically conductive and materially bonded manner in the contact area 131. Thus, the vaporizer 60 is electrically and mechanically bonded and retained to the carrier 4 via the contact area 131.

The vaporizer 60 comprises a rectangular base surface with two opposing edge sections 132a, 132b. The vaporizer 60 is connected to one of the electrical lines 105a, 105b in each of the edge sections 132a, 132b. The electrical lines 105a, 105b each extend from the contact area 131 to an end portion 205a, 205b. At the end portions 205a, 205b, the vaporizer device 1 is contactable for supplying the vaporizer 60 with electrical energy from an external part, for example a heating voltage source 71. The end portions 205a, 205b are advantageously formed for soldering to a contact of the external part or together with the carrier 4 as a connector.

The end portions 205a, 205b are advantageously arranged at an end 122 of the carrier 4 located upstream of the vaporizer 60 for supplying electric energy to the vaporizer 60. The end 122 located upstream of the vaporizer 60 is the end arranged for mechanical and/or electrical connection to an external part, for example a base part 16 of the inhaler 10, by means of the electrical contacting. The electrical lines 105a, 105b preferably run parallel to the air channel 130.

Between the electrical lines 105a, 105b, the carrier comprises a passage opening 104. The passage opening 104 is arranged at the inlet side 61 of the vaporizer 60. Advantageously, the passage opening 104 is arranged between the contact areas 131 of the electrical lines 105a, 105b. A wick structure 19 can extend through the passage opening 104 to contact the inlet side 61 of the vaporizer in a liquid-conducting manner. The passage opening 104 advantageously comprises a shape corresponding to the shape of the wick structure 19.

A plurality of solder bumps 150 are optionally provided on the electrical lines 105a, 105b in the contact area 131. The solder bumps 150 are advantageously made of gold and can provide an electrically conductive bond between the vaporizer 60 and the electrical lines 105a, 105b, for example, by means of thermocompression.

To mechanically and/or thermally improve the bond between the electrical lines 105a, 105b and the vaporizer 60, the bond may comprise an adhesive. In particular, the adhesive may be electrically non-conductive so as not to interfere with the electrically conductive bond. Advantageously, the adhesive comprises a low thermal conductivity to reduce the heat input from the vaporizer 60 into the carrier 4.

To produce the vaporizer devices 1 shown in FIGS. 1 and 2, the carrier 4 with the electrical lines 105a, 105b and the vaporizer 60 are provided.

The vaporizer 60 may be provided in a wafer compound from which a plurality of vaporizers 60 are fabricated. The plurality of vaporizers 60 is fabricated, for example, by various etching and coating processes, particularly by structuring the wafer compound by fabricating the liquid channels 62.

The vaporizer 60 may be provided with a metallization layer 133 in preparation for bonding to the electrical lines 105a, 105b. The metallization layer 133 may be applied directly to the vaporizer 60 or to a primer, such as a seed layer of aluminum. The metallization layer 133 may comprise currentlessly deposited nickel, gold, and/or palladium, or a material composite thereof. This may happen simultaneously for a plurality of vaporizers 60, for example a wafer compound, to parallelize the process.

Optionally, the solder bumps 150 can be applied to the surface of the vaporizer 60 or to its metallization layer 133 and/or to the electrical lines 105a, 105b or to the surface of the advantageously ceramic carrier 4 in the contact area 131. Advantageously, a layer of gold is applied to each of the electrical lines 105a, 105b in the contact area 131 for this purpose. The solder bumps 150 can be arranged thereon.

Alternatively, a sintering paste suitable for the material bond is printed and/or applied either to the electrical lines 105a, 105b of the advantageously ceramic carrier 4 or to a designated contact area of the vaporizer 60.

Subsequently, the wafer compound is singulated, thereby providing a plurality of vaporizers 60. The singulated vaporizers 60 are removed from the wafer compound, for example, by means of a picking process. By means of flip-chip assembly, the vaporizers 60 are bonded to the electrical lines 105a, 105b of the advantageously ceramic carrier 4 using a thermocompression process. The thermocompression process can be enhanced by the application of ultrasound through an introduction of friction welding heat. Optionally, the compound of vaporizer 60 and carrier 4 can be mechanically stabilized by an electrically non-conductive adhesive.

In this case, the carriers 4 may be in a carrier compound on which the plurality of vaporizers 60 are arranged and applied. After the vaporizers 60 have been fitted and connected to the carriers 4 in the carrier compound, the vaporizer devices 1 thus produced can be separated.

The vaporizer devices 1 or rather the compounds of vaporizer 60 and carrier 4 are then placed between the two half-shells 108a, 108b. The carrier structure 400 can then be installed in a vaporizer insert 100, a consumption unit 17 and/or an inhaler 10.

In FIGS. 1 and 2, the electrically conductive and substance-to-substance compound of vaporizer 60 and carrier 4 is produced by a thermocompression process using solder bumps 150.

Figure 3:
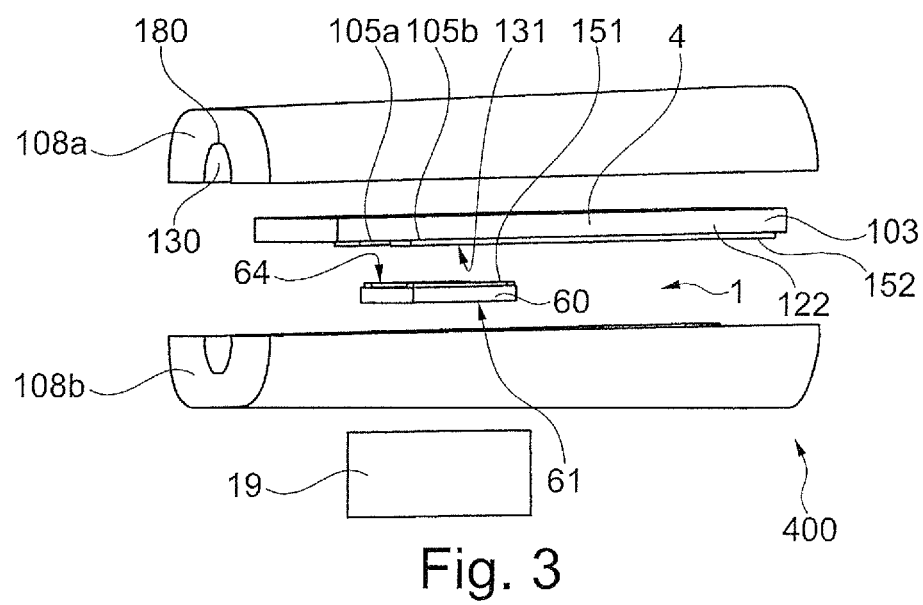
FIG. 3 an exploded view of a vaporizer device and a carrier device.
Figure 4:
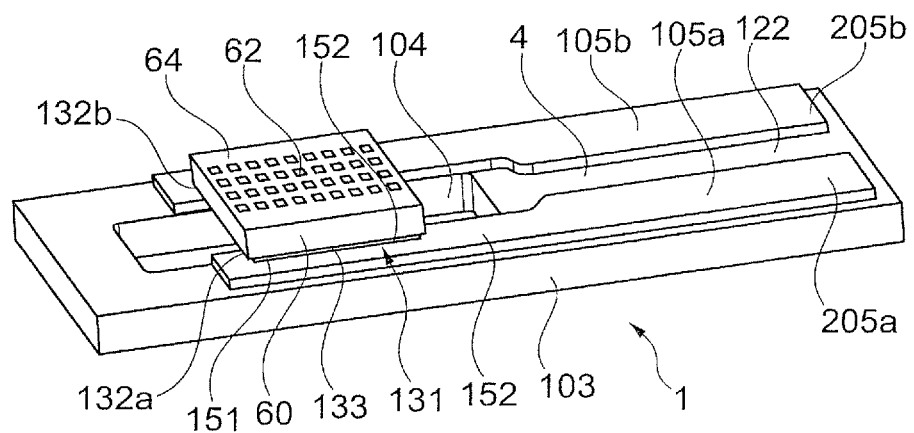
FIG. 4 a perspective view of a vaporizer device in the assembled state.

FIGS. 3 and 4 show an alternative to the bond shown in FIGS. 1 and 2 with the assistance of solder bumps 150 using sintered material 151, 152. FIGS. 3 and 4 are explained with regard to the differences from FIGS. 1 and 2.

FIG. 3 shows an exploded view of the vaporizer device 1 and the carrier device 400, wherein a first sintered material 151 is provided on the vaporizer 60 to form an electrically conductive and materially bonded connection with the electrical lines 105a, 105b. FIG. 4 shows a perspective view of the vaporizer device 1.

The contact area 131 of the electrical lines 105a, 105b on the carrier 4 and/or the contact area on the surface of the vaporizer 60 is arranged for sintering, in particular pressureless sintering, for example by a layer of gold.

The electrical lines 105a, 105b are made of a second sintered material 152. The second sintered material 152 is applied to the ceramic substrate 103 or the carrier 4 and forms the electrical lines 105a, 105b after sintering. Sintering will bond materially the second sintered material 152 and thus the electrical lines 105a, 105b to the carrier 4.

It is also possible that the first sintered material 151 consists of the same material as the second sintered material 152. In this case, in only one sintering process, the electrical lines 105a, 105b that are materially bonded to the carrier 4 and the bond between the vaporizer 60 and the electrical lines 105a, 105b can be produced at the same time.

Alternatively, the carrier 4 may be provided with electrical lines 105a, 105b already in place and only the material bond between the vaporizer 60 and the electrical lines 105a, 105b may be formed from the second sintered material 152.

For forming the bond with the first sintered material 151, it is unnecessary to apply solder bumps. For this purpose, a sintering paste suitable for sintering is advantageously either printed or applied to the electrical lines 105a, 105b of the advantageously ceramic carrier 4. After the vaporizers 60 have been singulated, the vaporizers 60 are placed on the first sintering material 151 on the electrical lines 105a, 105b.

Alternatively, the first sintered material 151 may be printed and/or applied to the intended contact surface of the vaporizer 60. After singulation the vaporizers 60, the vaporizers 60 are placed on the electrical lines 105a, 105b.

For a stable bond between the electrical contact area 131 and the vaporizer 60, the compound of the carrier 4 and the vaporizer 60 is sintered in a furnace with the first sintered material 151 and optionally with the second sintered material 152 for the electrical lines 105a, 105b.

Both the embodiments shown in FIGS. 1 and 2 and FIGS. 3 and 4 allow electrical contacting of the vaporizer 60 while maintaining low thermal conduction from the vaporizer 60 to the carrier 4. The electrical bond between the vaporizer 60 and the electrical line 105a, 105b comprises an electrical resistance of 5 mΩ to 20 mΩ. By adjusting the cross-section and/or length or thickness of the electrical bond, i.e. the solder bumps 150 and/or the first sintered material 151, the heat generated from the heat conduction from the vaporizer 60 and the heat generated by the electrical resistance between the electrical line 105a, 105b and the vaporizer 60, which is transferred into the carrier 4, is minimal.

Figure 5:
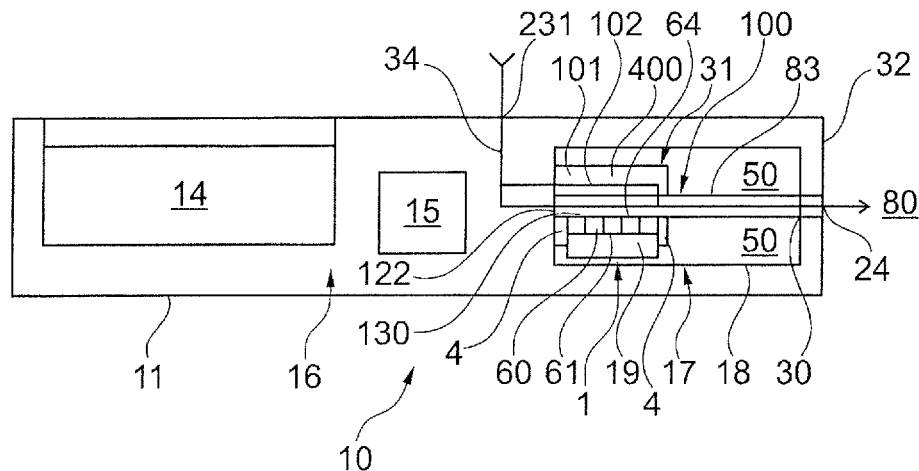
FIG. 5 a schematic view of an inhaler.

FIG. 5 schematically illustrates an inhaler 10 respectively an electronic cigarette product. The inhaler 10 includes a housing 11 in which an air flow channel 30 is provided between at least one air inlet opening 231 and an air outlet opening 24 at a mouth end 32 of the inhaler 10. The mouth end 32 of the inhaler 10 thereby denotes the end at which the consumer draws for the purpose of inhalation, thereby applying a negative pressure to the inhaler 10 and generating an airflow 34 in the airflow channel 30.

The inhaler 10 advantageously consists of a base part 16 and a consumption unit 17 or vaporizer tank unit, which comprises the vaporizer device 1 and the liquid reservoir 18 and is designed in particular in the form of a replaceable cartridge. The air drawn in through the air inlet opening 231 is directed in the air flow channel 30 to, or through, the at least one vaporizer device 1. The vaporizer device 1 is connected or connectable to the liquid reservoir 18, in which at least one liquid 50 is stored.

The vaporizer device 1 vaporizes liquid 50, which is advantageously fed to the vaporizer device 1 from the liquid reservoir 18 by a wick or wick structure 19 by means of capillary forces, and adds the vaporized liquid as an aerosol/vapor to the air stream 34 at an outlet side 64.

At an inlet side 61 of the vaporizer 60, the porous and/or capillary liquid-conducting wick structure 19 is advantageously arranged, as shown schematically in FIG. 5. A liquid interface and/or several liquid lines may be provided between liquid reservoir 18 and wick structure 19. The liquid reservoir 18 can therefore also be arranged at a distance from the wick structure 19. The wick structure 19 advantageously contacts the inlet side 61 of the vaporizer 60 in a planar manner and covers all liquid channels 62 of the vaporizer 60 on the inlet side. On the side opposite the vaporizer 60, the wick structure is connected to the liquid reservoir 18 in a liquid-conducting manner. The liquid reservoir 18 may be larger in dimensions than the wick structure 19. For example, the wick structure 19 may be inserted into an opening of a housing of the liquid reservoir 18. A plurality of vaporizer devices 1 may also be associated with a liquid reservoir 18. The wick structure 19 may be generally one-piece or multi-piece.

The wick structure 19 comprises porous and/or capillary material which, due to capillary forces, is capable of passively feeding liquid vaporized by the vaporizer 60 from the liquid reservoir 18 to the vaporizer 60 in sufficient quantity to prevent the liquid channels 62 from running dry and resulting problems.

Advantageously, the wick structure 19 comprises an electrically non-conductive material to prevent undesirable heating of fluid in the wick structure 19 by current flow. The wick structure 19 advantageously comprises a low thermal conductivity. Advantageously, the wick structure 19 comprises one or more of the materials: cotton, cellulose, acetate, glass fiber fabric, glass fiber ceramic, sintered ceramic, ceramic paper, aluminosilicate paper, metal foam, metal sponge, another heat resistant, porous and/or capillary material having a suitable feed rate, or a composite of two or more of the foregoing materials. In an advantageous practical embodiment, the wick structure 19 may comprise at least one of a ceramic fiber paper and/or a porous ceramic. The volume of the wick structure 19 is preferably in the range between 1 $mm^3$ and 10 $mm^3$, further preferably in the range between 2 $mm^3$ and 8 $mm^3$, still further preferably in the range between 3 $mm^3$ and 7 $mm^3$ and is for example 5 $mm^3$.

If the wick structure 19 is made of an electrically and/or thermally conductive material, an insulating layer of an electrically and/or thermally insulating material, for example glass, ceramic or plastic, is advantageously provided between the wick structure 19 and the vaporizer 60, with openings extending through the insulating layer and corresponding to the liquid channels 62.

An advantageous volume of the liquid reservoir 18 is in the range between 0.1 ml and 5 ml, preferably between 0.5 ml and 3 ml, further preferably between 0.7 ml and 2 ml or 1.5 ml.

The electronic cigarette 10 further comprises an electrical energy storage device 14 and an electronic control device 15. The energy storage device 14 is generally arranged in the base part 16 and may in particular be a disposable electrochemical battery or a rechargeable electrochemical battery, for example a lithium-ion battery. The consumption unit 17 is arranged between the energy storage device 14 and the mouth end 32. The electronic control device 15 comprises at least one digital data processing device, in particular microprocessor and/or microcontroller, in the base part 16 (as shown in FIG. 5) and/or in the consumption unit 17 or a vaporizer insert 100.

A sensor, for example a pressure sensor or a pressure or flow switch, is advantageously arranged in the housing 11, wherein the control device 15 can determine, based on a sensor signal output by the sensor, that a consumer is drawing on the mouth end 32 of the inhaler 10 to inhale. In this case, the control device 15 controls the vaporizer device 1 to add liquid 50 from the liquid reservoir 18 as an aerosol/vapor into the air flow 34.

The vaporizer device 1 or the at least one vaporizer 60 is arranged in a part of the consumption unit 17 facing away from the mouth end 32. This enables effective electrical coupling and control of the vaporizer device 1. Advantageously, the air flow 34 passes through an air flow channel 30 extending axially through the liquid reservoir 18 to the air outlet opening 24.

The liquid 50 stored in the liquid reservoir 18 to be dispensed is, for example, a mixture of 1,2-propylene glycol, glycerol, water, at least one aroma (flavor) and/or at least one active ingredient, in particular nicotine. However, the indicated components of the liquid 50 are not mandatory. In particular, flavoring and/or active ingredients, in particular nicotine, may be omitted.

The consumption unit or cartridge 17 or the base part 16 advantageously comprises a non-volatile data memory for storing information or parameters relating to the consumption unit or cartridge 17. The data memory can be part of the electronic control device 15. The data memory advantageously stores information on the composition of the liquid stored in the liquid reservoir 18, information on the process profile, in particular power/temperature control; data on condition monitoring or system testing, for example leak testing; data relating to copy protection and counterfeit protection, an ID for unambiguous identification of the consumption unit or cartridge 17, serial number, date of manufacture and/or expiration date, and/or number of draws (number of inhalation draws by the consumer) or the time of use. The data memory is advantageously electrically connected or connectable to the control device 15.

In the inhaler 10 and/or in an external memory which can be connected to the inhaler 10 in a suitable and well-known manner, at least temporarily, in terms of communication technology, user-related data, in particular about smoking behavior, could also be stored and preferably also used for controlling and regulating the inhaler.

A vaporizer insert 100 is provided for insertion into the liquid reservoir 18. For this purpose, the liquid reservoir comprises at least one insertion opening into which the vaporizer insert 100 can be inserted, in particular pushed in. The vaporizer insert 100 comprises a base component 83 for receiving the carrier device 400, the carrier 4 and the vaporizer 60. The base component 83 comprises a jacket side 31 which encloses the air flow channel 30 through which the air flow 34 can flow.

The base component 83 is liquid-tight and does not allow liquid 50 to penetrate into the interior of the vaporizer insert 100, in order to prevent unwanted leakage of liquid 50 from the air flow channel 30 and/or the consumption unit 17. The sealing of the vaporizer insert 100 is such that liquid 50 can only take the path through the wick structure 19 and subsequently through the vaporizer 60 and is added to the airflow 34 in the vaporized state.

The air channel 130 formed by the carrier device 400 in the region of the vaporizer 60 merges into the air flow channel 30 downstream of the vaporizer 60. The air channel 130 can be understood as the flow portion of the air flow channel 130 formed by carrier device 400.

Additional channels, in particular at least one secondary air channel 101, which meet the air channel 130 and/or the air flow channel 130 downstream of the vaporizer 60, can provide for mixing of the gas/aerosol mixture with fresh air from a secondary air flow 102 and/or regulate processes of post-treatment and/or recondensation.

Figure 6:
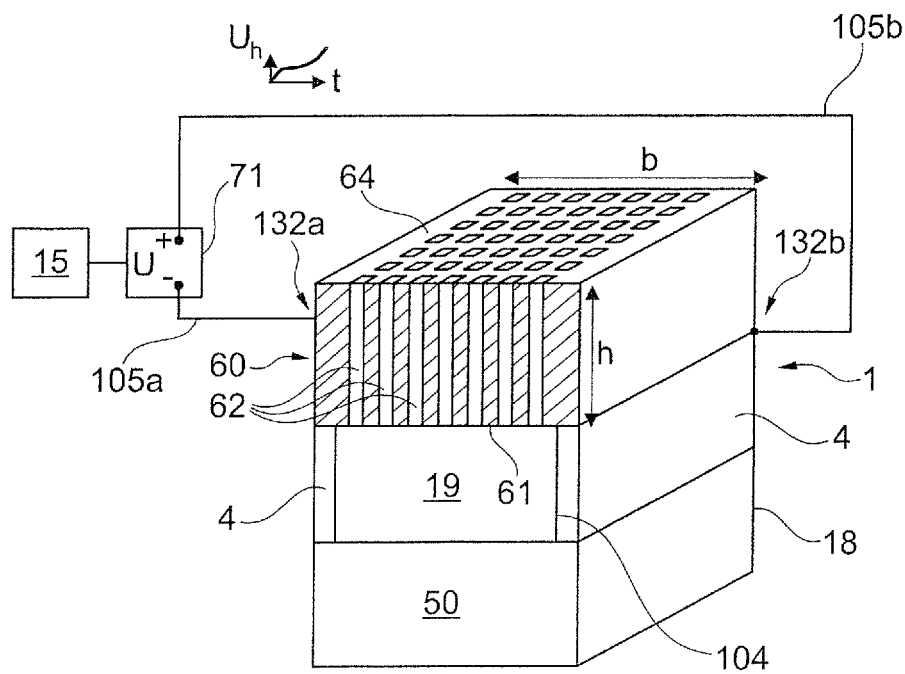
FIG. 6 a perspective section through a vaporizer device.

The vaporizer device 1 according to FIG. 6 comprises a block-shaped, preferably monolithic heating body respectively vaporizer 60 preferably made of an electrically conducting material, in particular a semiconductor material preferably silicon, and a carrier 4 with a passage opening 104 for the liquid-conducting connection of the vaporizer 60 and a liquid reservoir 18. For this purpose, a wick structure 19 is advantageously arranged in the passage opening 104.

It is not necessary that the entire vaporizer 60 is made of an electrically conductive material. It may be sufficient, for example, that the surface of the vaporizer 60 is electrically conductive, for example metallic, coated or preferably suitably doped. In this case, the entire surface need not be coated, for example metallic or preferably non-metallic or non-metallically clad metallic conductive tracks may be provided on a non-conductive or semi-conductive base body. It is also not essential that the entire vaporizer 60 heats; for example, it may be sufficient if a section or heating layer of the vaporizer 60 heats in the region of the outlet side 64.

Advantageously, the vaporizer 60 comprises a metallization layer 133 on at least one contact surface provided for electrical contacting.

The vaporizer 60 is provided with a plurality of microchannels or liquid channels 62 which connect an inlet side 61 of the vaporizer 60 to an outlet side 64 of the vaporizer 60 in a liquid-conducting manner. The inlet side 61 is connected in a liquid-conducting manner to the liquid reservoir 18 via a wick structure 19 not shown in FIG. 6. The wick structure 19 serves to passively feed liquid from the liquid reservoir 18 to the vaporizer 60 by means of capillary forces.

The average diameter of the liquid channels 62 is preferably in the range between 5 µm and 200 µm, further preferably in the range between 30 µm and 150 µm, still further preferably in the range between 50 µm and 100 µm. Due to these dimensions, a capillary effect is advantageously created so that liquid entering a liquid channel 62 at the inlet side 61 rises upward through the liquid channel 62 until the liquid channel 62 is filled with liquid. The volume ratio of liquid channels 62 to vaporizer 60, which may be referred to as the porosity of vaporizer 60, is for example in the range between 10% and 50%, advantageously in the range between 15% and 40%, still further advantageously in the range between 20% and 30%, and is for example 25%.

The edge lengths of the areas of the vaporizer 60 provided with liquid channels 62 are for example in the range between 0.5 mm and 3 mm, preferably between 0.5 mm and 1 mm. The dimensions of the areas of the vaporizer 60 provided with liquid channels 62 may be, for example: 0.95 mm×1.75 mm or 1.9 mm×1.75 mm or 1.9 mm×0.75 mm. The edge lengths of the vaporizer 60 may be, for example, in the range between 0.5 mm and 5 mm, preferably in the range between 0.75 mm and 4 mm, further preferably in the range between 1 mm and 3 mm. The area of the vaporizer 60 (chip size) may be, for example, 1 mm×3 mm, 2 mm×2 mm or 2 mm×3 mm.

The width b of the vaporizer 60 (see FIG. 6) is preferably in the range between 1 mm and 5 mm, further preferably in the range between 2 mm and 4 mm, and is for example 3 mm. The height h of the vaporizer 60 (see FIG. 6) is preferably in the range between 0.05 mm and 1 mm, further preferably in the range between 0.1 mm and 0.75 mm, still further preferably in the range between 0.2 mm and 0.5 mm, and is for example 0.3 mm. Even smaller vaporizers 60 can also be manufactured, provided and functionally operated The number of liquid channels 62 preferably is in the range between four and 1000. In this way, the heat input into the liquid channels 62 can be optimized and an ensured high vaporization performance as well as a sufficiently large vapor outlet area can be realized.

The liquid channels 62 are arranged in the form of a square, rectangular, polygonal, round, oval or otherwise shaped array. The array may be in the form of a matrix with s columns and z rows, wherein s is advantageously in the range between 2 and 50 and further advantageously in the range between 3 and 30 and/or z is advantageously in the range between 2 and 50 and further advantageously in the range between 3 and 30. In this way, an effective and easily producible arrangement of the liquid channels 62 with an ensured high vaporization performance can be realized.

The cross-section of the liquid channels 62 may be square, rectangular, polygonal, round, oval or otherwise shaped, and/or may change section-wise in the longitudinal direction, in particular increase, decrease or remain constant.

The length of one or each fluid channel 62 is preferably in the range between 100 μm and 1000 μm, further preferably in the range between 150 μm and 750 μm, still further preferably in the range between 180 μm and 500 μm and is for example 300 μm. In this way, optimum liquid absorption and portion formation can be achieved with sufficiently good heat input from the vaporizer 60 into the liquid channels 62.

The distance between two liquid channels 62 is preferably at least 1.3 times the clear diameter of a liquid channel 62, wherein the distance is related to the center axes of the two liquid channels 62. The distance can preferably be 1.5 to 5 times, more preferably 2 to 4 times, the clear diameter of a liquid channel 62. In this way, an optimal heat input into the vaporizer 60 and a sufficiently stable arrangement and wall thickness of the liquid channels 62 can be realized.

Based on the features described above, the vaporizer 60 can also be referred to as a volume heater.

The vaporizer device 1 comprises a heating voltage source 71 which is preferably controllable by the control device 15 and is connected to the vaporizer 60 via electrical lines 105a, 105b in a contact area 131 (not shown in FIG. 6) at opposite edge portions 132a, 132b of the vaporizer 60, so that an electrical voltage Uh generated by the heating voltage source 71 results in a current flow through the vaporizer 60. Due to the ohmic resistance of the electrically conductive vaporizer 60, the current flow causes heating of the vaporizer 60 and therefore vaporization of liquid contained in the liquid channels 62. Vapor/aerosol 6 generated in this way escapes to the outlet side 64 from the liquid channels 62 and is mixed with the air flow 34. More precisely, when an airflow 34 caused by drawing of the consumer through the air flow channel 30 is detected, the control device 15 controls the heating voltage source 71, whereby the liquid contained in the liquid channels 62 is driven out of the liquid channels 62 in the form of vapor/aerosol by spontaneous heating.

An electronic or electrical connection of the vaporizer 60 to the electrical lines 105a, 105b is explained with reference to FIGS. 1 to 4.

Preferably, a voltage curve Uh(t) adapted to the liquid mixture used is stored in the data memory of the inhaler 10. This makes it possible to specify the voltage curve Uh(t) adapted to the liquid used, so that the heating temperature of the vaporizer 60, and thus also the temperature of the capillary liquid channels 62, can be controlled in time over the vaporization process in accordance with the known vaporization kinetics of the respective liquid, whereby optimum vaporization results can be achieved. The vaporization temperature is preferably in the range between 100° C. and 400° C., further preferably between 150° C. and 350° C., still further preferably between 190° C. and 290° C.

Advantageously, the vaporizer 60 can be made from portions of a wafer with thin film layer technology, which comprises a layer thickness preferably less than or equal to 1000 μm, further preferably 750 μm, still further preferably less than or equal to 500 μm. Surfaces of the vaporizer 60 may advantageously be hydrophilic. The outlet side 64 of the vaporizer 60 may advantageously be microstructured or comprise micro grooves.

The vaporizer device 1 is adjusted to add a quantity of liquid preferably in the range between 1 μl and 20 μl, further preferably between 2 μl and 10 μl, still further preferably between 3 μl and 5 μl, typically 4 μl per puff of the consumer.

Preferably, the vaporizer device 1 can be adjustable with respect to the amount of liquid/vapor per puff, i.e. per puff duration from 1 s to 3 s.

In the following, the sequence of the vaporization process is explained by way of example.

In an initial state, the voltage source 71 respectively the energy storage device 14 is switched off for the heating process.

To vaporize liquid 50, the voltage source 14, 71 for the vaporizer 60 is activated. The voltage Uh is set in such a way that the vaporization temperature in the vaporizer 60 and thus in the liquid channels 62 is adapted to the individual vaporization behavior of the liquid mixture used. This prevents the risk of local overheating and thus the formation of pollutants.

As soon as an amount of liquid has vaporized that corresponds to or is related to the volume of the liquid channels 62, the heating voltage source 71 is deactivated. Since the liquid properties and quantity are advantageously known exactly and the vaporizer 60 comprises a measurable temperature-dependent resistance, this point in time can be determined or controlled very precisely.

After completion of the heating process, the liquid channels 62 are predominantly or completely drained. The heating voltage 71 is then kept switched off until the liquid channels 62 are filled up again by means of the refeed of liquid through the wick structure 19. As soon as this is the case, the next heating cycle can be started by switching on the heating voltage 71.

The drive frequency of the vaporizer 60 generated by the heating voltage source 71 is generally advantageously in the range of 1 Hz to 50 kHz, preferably in the range of 30 Hz to 30 kHz, even more advantageously in the range of 100 Hz to 25 kHz.

The frequency and duty factor of the heating voltage Uh for the vaporizer 60 are advantageously adapted to the natural oscillation or natural frequency of the bubble oscillations during bubble boiling. Advantageously, the period 1/f of the heating voltage can therefore be in the range between 5 ms and 50 ms, further advantageously between 10 ms and 40 ms, still further advantageously between 15 ms and 30 ms, and for example 20 ms. Depending on the composition of the vaporized liquid 50, frequencies other than those mentioned can be optimally adapted to the natural oscillation or natural frequency of the bubble oscillations.

Furthermore, it has been shown that the maximum heating current generated by the heating voltage Uh should preferably be no more than 7 A, further preferably no more than 6.5 A, still further preferably no more than 6 A, and optimally in the range between 4 A and 6 A, in order to ensure concentrated vapor while avoiding overheating.

The feed rate of the wick structure 19 is again optimally adapted to that of the vaporization rate of the vaporizer 60, so that sufficient liquid 50 can be re-fed at any time and running empty of the area in front of the vaporizer 60 is avoided.

The vaporizer device 1 is preferably based on MEMS technology, in particular silicon, and therefore advantageously a micro-electro-mechanical system.

According to what has been said before, a layered structure is advantageously proposed consisting of a Si-based vaporizer 60, which is advantageously planar at least on the inlet side 61, and one or more underlying capillary structures 19 with advantageously different pore sizes. The wick structure 19 arranged directly on the inlet side 61 of the vaporizer 60 prevents the formation of bubbles on the inlet side 61 of the vaporizer 60, since gas bubbles prevent a further feeding effect and at the same time lead to a (local) overheating of the vaporizer 60 due to a lack of cooling by liquid flowing in.

Embodiments

Embodiment 1. Vaporizer device (1) for an inhaler (10), comprising
at least one electric vaporizer (60) for vaporizing liquid (50) fed to the vaporizer (60), wherein the liquid (50) is transported by capillary forces from an inlet side (61) through at least one liquid channel (62) to an outlet side (64), where vaporized liquid (50) can be added to an air flow (34),
a carrier (4) retaining the vaporizer (60), and
at least one electrical line (105a, 105b) electrically contacting the vaporizer (60), characterized in that
the electrical line (105a, 105b) comprises a planar contact area (131), and
the vaporizer (60) and the planar contact area (131) of the electrical line (105a, 105b) are bonded materially and electrically conductively to each other.

Embodiment 2. Vaporizer device (1) according to embodiment 1, characterized in that
the outer shape of the vaporizer (60) is block-shaped, and one side (61, 64) of the vaporizer (60) is bonded in a planar manner to the electrical line (105a, 105b).

Embodiment 3. Vaporizer device (1) according to one of the preceding embodiments, characterized in that
the vaporizer (60) comprises a base surface, in particular a rectangular base surface, with two opposing edge sections (132a, 132b), and each of the opposing edge sections (132a, 132b) is bonded to an electrical line (105a, 105b).

Embodiment 4. Vaporizer device (1) according to one of the preceding embodiments, characterized in that
the carrier (4) retains the electrical line (105a, 105b) and/or is materially bonded to the electrical line (105a, 105b).

Embodiment 5. Vaporizer device (1) according to one of the preceding embodiments, characterized in that
at least two electrical lines (105a, 105b) are provided, and the carrier (4) comprises a passage opening (104) between the electrical lines (105a, 105b).

Embodiment 6. Vaporizer device (1) according to one of the preceding embodiments, characterized in that
the carrier (4) comprises a ceramic substrate (103).

Embodiment 7. Vaporizer device (1) according to one of the preceding embodiments, characterized in that
the contact area (131) is made of gold.

Embodiment 8. Vaporizer device (1) according to one of the preceding embodiments, characterized in that
the vaporizer (60) comprises a metallization layer (133).

Embodiment 9. Vaporizer device (1) according to embodiment 8, characterized in that
the metallization layer (133) comprises nickel, gold and/or palladium.

Embodiment 10. Vaporizer device (1) according to embodiment 8 or 9, characterized in that
a primer is arranged between the vaporizer (60) and the metallization layer (133).

Embodiment 11. Vaporizer device (1) according to one of the preceding embodiments, characterized in that
the electrical bond between the vaporizer (60) and the electrical line (105) comprises an electrical resistance of 5 mΩ to 20 mΩ.

Embodiment 12. Vaporizer device (1) according to one of the preceding embodiments, characterized in that
the material bond is at least partially formed by a first sintered material (151).

Embodiment 13. Vaporizer device (1) according to one of the preceding embodiments, characterized in that
the electrical line (105) is at least partially formed by a second sintered material (152).

Embodiment 14. Vaporizer device (1) according to one of the preceding embodiments, characterized in that
the material bond between the vaporizer (60) and the electrical line (105) comprises an adhesive, in particular an electrically non-conductive adhesive.

Embodiment 15. Vaporizer device (1) according to one of the preceding embodiments, characterized in that
the vaporizer (60) and/or the contact area (131) comprises solder bumps (150).

Embodiment 16. Vaporizer device (1) according to one of the preceding embodiments, characterized in that
the electrical line (105a, 105b) comprises a coefficient of thermal expansion that differs by less than 10% from the coefficient of thermal expansion of the vaporizer (60).

Embodiment 17. Consumption unit (17) for an inhaler (10), comprising
a vaporizer device (1) according to any of the preceding embodiments, and
a liquid reservoir (18), wherein
the vaporizer device (1) is connected to the liquid reservoir (18) in a liquid-conducting manner.

Embodiment 18. Inhaler (10), comprising
a consumption unit (17) according to embodiment 17, and a base unit (16).

Embodiment 19. Method for manufacturing a vaporizer device (1) according to any of the preceding embodiments 1 to 16, comprising the following steps:
Providing the vaporizer (60), the carrier (4), and the at least one electrical line (105a, 105b), and
materially and electrically conductively bonding the vaporizer (60) and the electrical line (105a, 105b) in a planar contact area of the vaporizer (60).

Embodiment 20. Method according to embodiment 19, characterized in that
the bonding comprises a thermocompression process.

Embodiment 21. Method according to embodiment 19 or 10, characterized in that
the bonding comprises an application of ultrasound.

Embodiment 22. Method according to any of the preceding embodiments 18 to 21, characterized in that
the bonding comprises sintering in particular without pressure.

Embodiment 23. Method according to any one of the preceding embodiments 18 to 22, characterized in that
a plurality of simultaneously processed vaporizers (60) are separated prior to bonding.

Embodiment 24. Method according to any one of the preceding embodiments 18 to 23, characterized in that
a plurality of solder bumps (150) are applied prior to bonding.

Embodiment 25. Method according to one of the preceding embodiments 18 to 24, characterized in that
the bonding comprises an adhesive bonding with an in particular non-conductive adhesive.

The invention claimed is:

1. A vaporizer device for an inhaler, comprising:
an electric vaporizer for vaporizing liquid fed to the electric vaporizer, wherein the liquid is transported by capillary forces from an inlet side through at least one liquid channel to an outlet side, where vaporized liquid can be added to an air flow, a carrier retaining the vaporizer, and at least one electrical line electrically contacting the electric vaporizer, wherein the at least one electrical line comprises a planar contact area, wherein the electric vaporizer and the planar contact area of the at least one electrical line are bonded materially and electrically conductively to each other, wherein the vaporizer comprises a metallization layer, and wherein a primer is arranged between the electric vaporizer and the metallization layer.

2. The vaporizer device according to claim 1,
wherein an outer shape of the vaporizer is block-shaped, and
wherein one side of the electric vaporizer is bonded in a planar manner to the at least one electrical line.

3. The vaporizer device according to claim 1,
wherein the electric vaporizer comprises a base surface, with two opposing edge sections, and each of the opposing edge sections is bonded to an electrical line of the at least one electrical line.

4. The vaporizer device according to claim 1,
wherein the carrier retains the at least one electrical line and/or is materially bonded to the at least one electrical line.

5. The vaporizer device according to claim 1,
wherein the at least one electrical line comprises at least two electrical lines, and wherein the carrier comprises a passage opening between the at least two electrical lines.

6. The vaporizer device according to claim 1,
wherein the carrier comprises a ceramic substrate.

7. The vaporizer device according to claim 1,
wherein the contact area is made of gold.

8. The vaporizer device according to claim 1,
wherein the metallization layer comprises nickel, gold and/or palladium.

9. The vaporizer device according to claim 1,
wherein an electrical bond between the electric vaporizer and the at least one electrical line comprises an electrical resistance of 5 m$\Omega$ to 20 m$\Omega$.

10. The vaporizer device according to claim 1,
wherein a material bond between the electric vaporizer and the at least one electrical line is at least partially formed by a first sintered material.

11. The vaporizer device according to claim 1,
wherein the at least one electrical line is at least partially formed by a second sintered material.

12. The vaporizer device according to claim 1,
wherein a material bond between the electric vaporizer and the at least one electrical line comprises an electrically non-conductive adhesive.

13. The vaporizer device according to claim 1,
wherein the electric vaporizer and/or the planar contact area comprises solder bumps.

14. The vaporizer device according to claim 1,
wherein the at least one electrical line comprises a coefficient of a first thermal expansion that differs by less than 10% from a second coefficient of thermal expansion of the electric vaporizer.

15. A consumption unit for an inhaler, comprising:
a vaporizer device according to claim 1, and
a liquid reservoir, wherein the electric vaporizer device is connected to the liquid reservoir in a liquid-conducting manner.

16. An inhaler, comprising:
a consumption unit according to claim 15, and
a base unit.

17. A method for manufacturing a vaporizer device according to claim 1, comprising the following steps:
providing the electric vaporizer, the carrier, and the at least one electrical line, and materially and electrically conductively bonding the electric vaporizer and the at least one electrical line in a planar contact area of the at least one electrical line.

18. The method according to claim 17,
wherein the materially and electrically conductively bonding comprises a thermocompression process, an application of ultrasound, sintering without pressure, and/or an adhesive bonding with a non-conductive adhesive.

19. The method according to claim 17,
wherein a plurality of simultaneously processed electric vaporizers are separated prior to materially and electrically conductively bonding.

20. The method according to claim 17,
wherein a plurality of solder bumps are applied prior to materially and electrically conductively bonding.

21. The method according to claim 17,
wherein the materially and electrically conductively bonding comprises an adhesive bonding with a non-conductive adhesive.

22. A vaporizer device for an inhaler, comprising:
an electric vaporizer for vaporizing liquid fed to the electric vaporizer, wherein the liquid is transported by capillary forces from an inlet side through at least one liquid channel to an outlet side, where vaporized liquid can be added to an air flow,
a carrier retaining the vaporizer, and
at least one electrical line electrically contacting the electric vaporizer,
wherein the at least one electrical line comprises a planar contact area,
wherein the electric vaporizer and the planar contact area of the at least one electrical line are bonded materially and electrically conductively to each other, and
wherein a material bond between the electric vaporizer and the at least one electrical line is at least partially formed by a first sintered material.

23. A vaporizer device for an inhaler, comprising:
an electric vaporizer for vaporizing liquid fed to the electric vaporizer, wherein the liquid is transported by capillary forces from an inlet side through at least one liquid channel to an outlet side, where vaporized liquid can be added to an air flow,
a carrier retaining the vaporizer, and
at least one electrical line electrically contacting the electric vaporizer,
wherein the at least one electrical line comprises a planar contact area,
wherein the electric vaporizer and the planar contact area of the at least one electrical line are bonded materially and electrically conductively to each other, and
wherein the at least one electrical line is at least partially formed by a second sintered material.

24. A vaporizer device for an inhaler, comprising:
an electric vaporizer for vaporizing liquid fed to the electric vaporizer, wherein the liquid is transported by capillary forces from an inlet side through at least one liquid channel to an outlet side, where vaporized liquid can be added to an air flow, a carrier retaining the vaporizer, and at least one electrical line electrically contacting the electric vaporizer, wherein the at least one electrical line comprises a planar contact area, wherein the electric vaporizer and the planar contact area of the at least one electrical line are bonded materially and electrically conductively to each other, and wherein a material bond between the electric vaporizer and the at least one electrical line comprises an electrically non-conductive adhesive.

* * * * *